US008853443B2

(12) United States Patent
Breuninger et al.

(10) Patent No.: US 8,853,443 B2
(45) Date of Patent: Oct. 7, 2014

(54) PROCESS FOR PREPARING AN ISOCYANATE

(75) Inventors: Daniel Breuninger, Bobenheim-Roxheim (DE); Johannes Adam, Dresden (DE); Heiner Schelling, Kirchheim (DE); Eckhard Stroefer, Mannheim (DE); Markus Kraemer, Radeburg (DE); Matthias Eiermann, Limburgerhof (DE); Kai Thiele, Antwerp (DE); Michael Zoellinger, Eislingen (DE); Rolf Pinkos, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 550 days.

(21) Appl. No.: 13/130,168

(22) PCT Filed: Nov. 18, 2009

(86) PCT No.: PCT/EP2009/065373
§ 371 (c)(1),
(2), (4) Date: Jul. 18, 2011

(87) PCT Pub. No.: WO2010/057909
PCT Pub. Date: May 27, 2010

(65) Prior Publication Data
US 2011/0263892 A1 Oct. 27, 2011

(30) Foreign Application Priority Data

Nov. 19, 2008 (EP) ..................................... 08169399

(51) Int. Cl.
C07C 263/00 (2006.01)
C07C 265/14 (2006.01)
C07C 263/10 (2006.01)

(52) U.S. Cl.
CPC .............. *C07C 263/10* (2013.01); *C07C 265/14* (2013.01)
USPC ............ 560/347; 560/330; 560/336; 560/338

(58) Field of Classification Search
CPC .. C07C 263/10; C07C 263/16; C07C 263/00; C07C 265/10
USPC .................................. 560/330, 336, 338, 347
See application file for complete search history.

(56) References Cited

U.S. PATENT DOCUMENTS

| 3,351,650 | A | * | 11/1967 | Metzger, Jr. et al. ......... 560/330 |
| 3,479,384 | A | | 11/1969 | Heiss |
| 3,725,478 | A | * | 4/1973 | Hanschke et al. ............ 564/306 |
| 4,189,354 | A | | 2/1980 | Ellendt et al. |
| 4,465,639 | A | | 8/1984 | Hatfield |
| 4,774,357 | A | | 9/1988 | Keggenhoff et al. |
| 5,362,914 | A | * | 11/1994 | Su .................................. 564/498 |
| 5,872,278 | A | | 2/1999 | Kraus et al. |
| 5,889,070 | A | | 3/1999 | Schilling et al. |
| 2012/0142960 | A1 | | 6/2012 | Bock et al. |

FOREIGN PATENT DOCUMENTS

| DE | 33 29 124 | 2/1985 |
| EP | 0 446 781 | 9/1991 |
| EP | 0 546 400 | 6/1993 |
| EP | 0 816 333 | 1/1998 |
| EP | 0 866 057 | 9/1998 |
| JP | 5-320296 A | 12/1993 |
| JP | 7-82223 A | 3/1995 |
| JP | 9-52873 A | 2/1997 |
| JP | 10-306068 A | 11/1998 |
| JP | 2004-529115 A | 9/2004 |
| JP | 2006-104166 A | 4/2006 |

OTHER PUBLICATIONS

U.S. Appl. No. 13/381,357, filed Dec. 22, 2011, Schelling, et al.
U.S. Appl. No. 13/380,680, filed Dec. 23, 2011, Schelling, et al.
U.S. Appl. No. 13/383,549, filed Jan. 11, 2012, Schelling, et al.
U.S. Appl. No. 13/383,433, filed Jan. 11, 2012, Schelling, et al.
Office Action issued Mar. 21, 2013 in Korean Patent Application No. 10-2011-7014007 English translation only.
Ulrich, H., "Chemistry and Technology of Isocyanates", John Wiley & Sons, Total 6 Pages, (1996).
International Search Report Issued Apr. 22, 2010 in PCT/EP09/065373 filed Nov. 18, 2009.
U.S. Appl. No. 13/163,928, filed Jun. 20, 2011, Rosendahl, et al.
U.S. Appl. No. 13/266,049, filed Oct. 24, 2011, Stroefer, et al.
Japanese Office Action Issued May 14, 2013 in Patent Application No. 2011-536849 (English translation only).

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a process for preparing an isocyanate, comprising hydrogenating a mixture (Gi) comprising an amine in the presence of a hydrogenation catalyst comprising copper to obtain a mixture (Gii) comprising the amine, and reacting the mixture (Gii) with phosgene to obtain a mixture (Giii) comprising the isocyanate. The present invention further relates to the isocyanate preparable by this process.

18 Claims, No Drawings

PROCESS FOR PREPARING AN ISOCYANATE

The present invention relates to a process for preparing an isocyanate, comprising hydrogenating a mixture (Gi) comprising an amine in the presence of a hydrogenation catalyst comprising copper to obtain a mixture (Gii) comprising the amine, and reacting the mixture (Gii) with phosgene to obtain a mixture (Giii) comprising the isocyanate. The present invention further relates to the isocyanate preparable by the process according to the invention.

Isocyanates are very important raw materials for the preparation of polyurethanes. Of industrial importance are especially the di- and polyisocyanates of the diphenylmethane series (MDI). The general term "MDI", as used in the context of the present invention, refers to mixtures of diisocyanates and polyisocyanates of the diphenylmethane series.

A diisocyanate or a polyisocyanate of the diphenylmethane series refers to an isocyanate of the following type:

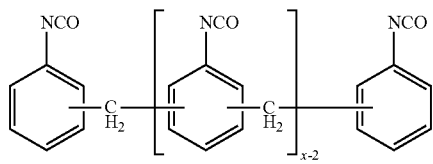

where x = 2 to n where n is an integer greater than 1, for example 2, 3, 4, 5, 6, 7, 8, 9, 10 or greater than 10. When it is a diisocyanate, n is 2. When it is a polyisocyanate, n is greater than 2.

It is known that MDI can be prepared by phosgenating MDA. The general term "MDA", as used in the context of the present invention, refers to mixtures of diamines and polyamines of the diphenylmethane series.

A diamine or a polyamine of the diphenylmethane series is understood to mean an amine of the following type:

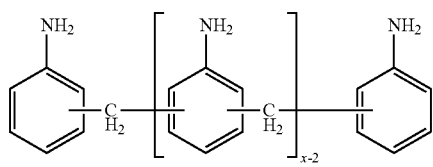

where x = 2 to n where n is an integer greater than 1, for example 2, 3, 4, 5, 6, 7, 8, 9, 10 or greater than 10. When it is a diamine, n is 2. When it is a polyamine, n is greater than 2.

MDI is typically synthesized in a two-stage process, wherein aniline is first reacted with formaldehyde to give MDA and the MDA is then reacted with phosgene in a second step. The phosgenation of MDA is known to those skilled in the art and is described, for example, in H. Ullrich "Chemistry and Technology of Isocyanates", John Wiley, 1996.

The phosgenation of MDA has the disadvantage that highly undesirable discoloration occurs in the course of phosgenation, which arises through reaction of impurities present in the MDA with phosgene, and which is preserved in the course of further processing of the MDI to the polyurethanes. A further problem which is disadvantageous for the quality of the MDI is the contamination of the MDI by chlorinated components.

Numerous methods are known for empirical lightening of the color of MDI. In order to reduce the level of the undesired discoloration mentioned, for example, DE-A 33 29 124 and U.S. Pat. No. 3,479,384 propose working up the MDI obtained from the phosgenation by extractive purification methods.

U.S. Pat. No. 4,189,354 proposes the use of additional distillation steps to purify the MDI mixtures, as a result of which smaller amounts of chlorinated components and hence smaller amounts of hydrolyzable chlorine are said to remain in the MDI as an impurity. The smaller amount of chlorinated components is said to improve the quality of the polyurethanes prepared from the MDI.

EP-A 0 816 333 describes a process for preparing MDI, wherein a solution comprising at least one isocyanate, after the phosgenation and before the complete removal of the solvent, is subjected to a treatment with hydrogen in the presence of catalysts comprising transition metal compounds of groups I, VII and VIII. Explicitly disclosed are only catalysts comprising noble metals, especially palladium, platinum, rhodium and ruthenium.

An alternative process for lightening the color of MDI is described in U.S. Pat. No. 4,465,639. Here, lightening of the color of MDI is achieved by treating the reaction solution with water directly after the phosgenation of MDA and before the removal of the excess phosgene. Although the complex workup step of the above processes is dispensed with, the discoloration is not prevented here either, and has to be reduced by an aftertreatment of the MDI with water. This water treatment leads in turn to corrosion problems owing to the hydrogen chloride which forms.

The above-described processes have the disadvantage that the discoloration which arises in the course of phosgenation, i.e. the formation of the constituents which cause the discoloration, is not prevented, but the discoloration, once formed, or at least a portion of this discoloration which has formed, is instead only removed subsequently. For this removal, complicated additional workup and disposal steps may be necessary.

According to EP-A 0 866 057, an improvement in the quality of MDI is achieved not by removing the discoloration already formed, which is present in the MDI, but by treating the MDA precursor appropriately. The treatment consists in contacting the MDA with solid inorganic Lewis acids and/or Brønsted acids before the reaction thereof.

Instead of the treatment with Lewis acids, EP-A 0 446 781 proposes a treatment of MDA by hydrogenating the MDA with hydrogen in the presence of a hydrogenation catalyst. The hydrogenation catalysts described are catalysts which comprise platinum metals, and additionally nickels, metals or oxides of tungsten and molybdenum, or mixtures of different metals, for example nickel and molybdenum. The hydrogenated MDA is then reacted with phosgene to give MDI, which is said to have improved color number. Copper catalysts are not described.

EP-A 0 546 400 and U.S. Pat. No. 5,889,070 also describe processes for improving the color of MDA by hydrogenating the MDA in the presence of a metal catalyst. The metal catalysts mentioned are catalysts of group 8A, for example nickel, palladium, platinum, cobalt, ruthenium and rhodium.

The processes described in the prior art, which comprise additional purification steps, are very complicated and uneconomic as described above. The processes described in the prior art, in which additional purification steps are dispensed with, again have the disadvantage that usually very expensive catalysts are used for the hydrogenation and that these catalysts often promote side reactions which lead to chlorinated by-products in the MDA or in the MDI prepared therefrom. This leads to a disadvantageous increase in the chlorine values in the MDI.

Accordingly, there is still a need for novel processes for preparing isocyanates, especially for preparing isocyanates of the diphenylmethane series, with advantageous quality. In the context of the present invention, the term "isocyanates with advantageously quality" are understood to mean isocyanates which have small amounts of coloring substances and a small content of chlorinated components.

It was accordingly an object of the present invention to provide a novel process for preparing an isocyanate, wherein the isocyanate has only small amounts of coloring components and a small content of chlorine or chlorinated components.

This object is achieved, surprisingly, by a process for preparing an isocyanate, comprising
(i) hydrogenating a mixture (Gi) comprising an amine in the presence of a hydrogenation catalyst comprising copper to obtain a mixture (Gii) comprising the amine;
(ii) reacting the mixture (Gii) with phosgene to obtain a mixture (Giii) comprising the isocyanate.

Surprisingly, by virtue of the use of hydrogenation catalysts comprising copper in (i), a mixture comprising the isocyanate is obtained, which both comprises smaller amounts of coloring substances and has smaller chlorine values than an isocyanate prepared with other metal catalysts.

The present invention further relates to the isocyanate preparable by this process.

The wording "preparable by a process", as used in the context of the present application, comprises both the wording "preparable by a process" and the wording "prepared by a process".

The term "amine", as used in the context of the invention, refers to at least one polyamine or at least one diamine or a mixture of at least one polyamine and at least one diamine. Accordingly, the "amine" is, for example, a diamine, or a polyamine, or a mixture of a diamine and a polyamine, or a mixture of at least two diamines, for example of 2, 3, 4, 5 or 6 diamines, or a mixture of at least two polyamines, for example 2, 3, 4, 5 or 6 polyamines, or a mixture of a diamine and of at least two polyamines, or a mixture of at least two diamines and of a polyamine, or of a mixture of at least two diamines and at least two polyamines.

When the amine comprises at least one diamine, the at least one diamine is preferably selected from the group consisting of hexamethylenediamines, isophoronediamine, cyclohexyldiamines, phenyldiamines, tolyldiamines, naphthylenediamines, diphenylmethanediamines, dicyclohexylmethanediamine, and of mixtures of two or more of these compounds.

More preferably, the at least one diamine is selected from the group consisting of 1,6-hexamethylenediamine, isophoronediamine, cyclohexyldiamines, 2,4-tolylenediamine, 2,6-tolylenediamine, 1,5-naphthylenediamine, 2,2'-diphenylmethanediamine, 2,4'-diphenylmethanediamine, 4,4'-diphenylmethanediamine and mixtures of two or more of these compounds.

When the diamine comprises two or more diamines, the two or more diamines are preferably mutually isomeric diamines.

The at least one diamine is more preferably a diamine of the diphenylmethane series, especially a diamine selected from the group consisting of 2,2'-diphenylmethanediamine, 2,4'-diphenylmethanediamine and 4,4'-diphenylmethanediamine, and mixtures of two or more of these compounds.

When the amine comprises at least one polyamine, the at least one polyamine is preferably a polycyclic or higher molecular weight derivative of one of the abovementioned diamines or of mixtures of two or more of these compounds. The at least one polyamine is more preferably a polyamine of the diphenylmethane series.

In a preferred embodiment, the amine is selected from the group consisting of a diamine of the diphenylmethane series, a mixture of at least two diamines of the diphenylmethane series, a polyamine of the diphenylmethane series, a mixture of at least two polyamines of the diphenylmethane series, and a mixture of at least one diamine of the diphenylmethane series with at least one polyamine of the diphenylmethane series.

More preferably, the amine is a mixture of at least two diamines of the diphenylmethane and at least two polyamines of the diphenylmethane series.

Accordingly, the present invention also describes a process as described above, wherein the amine is a mixture of at least two diamines of the diphenylmethane series and at least two polyamines of the diphenylmethane series. The present invention further describes the polyisocyanate preparable by this process.

The amine is more preferably a mixture at least comprising the 2,2'-diphenylmethanediamine, 2,4'-diphenylmethanediamine and 4,4'-diphenylmethanediamine isomers, which are also referred to in the context of the invention as 2-ring MDA or as a monomer MDA or MMDA, and further comprising at least one polyamine of the diphenylmethane series. The at least one polyamine is, for example, a 3-ring MDA, i.e. an amine of the following formula where n is 3, or a higher oligomer, i.e. an amine of the following formula where n is greater than 3.

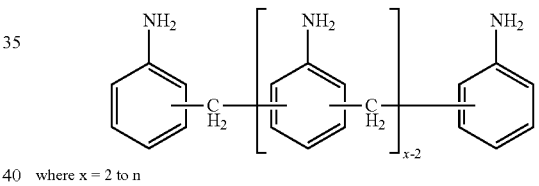

where x = 2 to n

The term "3-ring MDA" includes all possible isomeric forms of the formula below where n equals 3. Equally, the term "oligomer" comprises all isomeric forms of the individual higher polycyclic oligomers.

Accordingly, the present invention also describes a process as described above, wherein the amine is a mixture of 2,2'-diphenylmethanediamine, 2,4'-diphenylmethanediamine, 4,4'-diphenylmethanediamine, and of at least one polyamine of the diphenylmethane series.

In a preferred embodiment of the present invention, the amine used in (i) comprises a mixture of 2,2'-diphenylmethanediamine, 2,4'-diphenylmethanediamine and 4,4'-diphenylmethanediamine in an amount in the range from 1 to 100, more preferably from 20 to 90% by weight, more preferably from 30 to 80% by weight, more preferably from 40 to 75% by weight, and especially preferably from 55 to 70% by weight, based in each case on the total weight of the amine. The particular proportions of the individual isomers may vary.

In one embodiment of the invention, the amine comprises 2,2'-diphenylmethanediamine in an amount in the range from 0 to 1% by weight, for example 0.0001 to 1% by weight, 2,4'-diphenylmethanediamine in an amount in the range from 4 to 10% by weight, and 4,4'-diphenylmethanediamine in an amount in the range from 40 to 70% by weight.

When the amine comprises at least one polyamine of the diphenylmethane series, the former preferably comprises the latter in an amount in the range of up to 100% by weight, preferably 1 to 90% by weight, more preferably in an amount in the range from 10 to 80% by weight and especially preferably in an amount in the range from 20 to 55% by weight, based in each case on the total weight of the amine. When the amine comprises two or more polyamines, the percentages by weight are based on the sum of the polyamines based on the total weight of the amine. The particular proportions of the individual polyamines may vary. In one embodiment of the invention, the amine comprises 3-ring MDA in an amount in the range from 15 to 30% by weight and has a proportion of higher oligomers in an amount in the range from 5 to 25% by weight.

In a preferred embodiment, the amine comprises 2,2'-diphenylmethanediamine in an amount in the range from 0 to 1% by weight, for example 0.0001 to 1% by weight, 2,4'-diphenylmethanediamine in an amount in the range from 4 to 10% by weight, and 4,4'-diphenylmethanediamine in an amount in the range from 40 to 70% by weight, amine 3-ring MDA in an amount in the range from 15 to 30% by weight, and higher oligomers within a range from 5 to 25% by weight, based in each case on the total weight of the amine.

Provision of the Amine

The composition of the amine typically arises from the method of provision. In general, the amine can be provided in any manner known to those skilled in the art.

When the amine, in accordance with the preferred embodiment described above, is at least one diamine and/or at least one polyamine of the diphenylmethane series, the amine is preferably provided by reacting aniline with formaldehyde.

The formaldehyde can be supplied to the process according to the invention in the form of aqueous formaldehyde or in the form of higher homologs, so-called poly(oxy)methylene glycols or paraformaldehyde or trioxane, but also other formaldehyde precursors, for example methylal. The formaldehyde is preferably used as an aqueous solution.

When the formaldehyde is used as an aqueous solution, it preferably has a water content in the range from 1 to 95% by weight, more preferably from 25 to 90% by weight, more preferably from 40% by weight to 80% by weight and especially preferably from 50 to 70% by weight, based in each case on the total weight of the aqueous solution.

With regard to the aniline used in the reaction with formaldehyde, there are generally no restrictions. Typically, the aniline is prepared on the industrial scale from benzene by nitration and hydrogenation.

In the reaction to provide the amine, preferably a molar ratio of aniline to formaldehyde in the range from 20:1 to 1:1, more preferably in the range from 10:1 to 1.5:1, more preferably in the range from 4:1 to 1.75:1 and especially preferably in the range from 2.5:1 to 1.8:1 is used.

In the course of the present invention, this reaction is effected preferably in the presence of an acidic catalyst.

Accordingly, the present invention also relates to a process as described above, wherein the amine is prepared by reacting aniline and formaldehyde in the presence of an acidic catalyst. The present invention further relates to an isocyanate preparable by this process.

Preferred catalysts which are used in the context of the invention for reaction of aniline with formaldehyde are homogeneous acids, especially mineral acids, for example hydrochloric acid, sulfuric acid, methanesulfonic acid and phosphoric acid, and heterogeneous acids, for example acidic zeolites, ion exchangers, clays and polyacids. It is equally possible to use mixtures of two or more of the abovementioned acids. The use of hydrochloric acid as a catalyst is particularly preferred. When the catalyst used is hydrochloric acid, the acid can also be used in the form of gaseous hydrogen chloride. The amount of catalyst is preferably selected so as to give rise to a molar ratio of catalyst to aniline in the range from 0.01:1 to 1:1, preferably in the range from 0.05:1 to 0.5:1 and more preferably in the range from 0.08:1 to 0.3:1.

In addition, the reaction can be performed in the presence of a solvent. The reaction is preferably performed in a solvent selected from the group consisting of water, dimethylformamide, alcohols, ethers, aromatics, aliphatic amines, aromatic amines and mixtures of two or more of these compounds. More preferably, the reaction is performed in a solvent selected from the group consisting of water, dimethylformamide, linear C1 to C18-alcohols, aliphatic amines, aromatic amines, tetrahydrofuran, diethyl ether, tert-butyl methyl ether, benzene, toluene, xylene, halogenated aromatics, for example mono- or dichlorobenzene, and mixtures of two or more of these compounds. When the solvent comprises an alcohol, it preferably comprises a linear or branched C1 to C18 alcohol. When the solvent comprises an amine, it preferably comprises an aromatic amine, more preferably the amine which is reacted with formaldehyde. In the context of the invention, the solvent used is more preferably water and/or an aromatic amine, preferably aniline, as the solvent.

In a particularly preferred embodiment, the reaction of aniline with formaldehyde to provide the amine is performed in an aqueous medium with hydrochloric acid as the catalyst.

In one embodiment of the invention, the amine is provided by mixing aniline, formaldehyde, the catalyst used and if appropriate the solvent in a suitable mixing apparatus, for example in a mixing pump, a nozzle or a static mixer, and converting them in a suitable reaction apparatus, for example in a tubular reactor, a stirred reactor or a reaction column. The reaction temperature is preferably in the range from 20 to 200° C., more preferably in the range from 25 to 170° C., more preferably in the range from 30 to 150° C. and especially preferably in the range from 40 to 140° C.

In an alternative embodiment, aniline is first mixed with the catalyst and if appropriate with a solvent in a suitable mixing apparatus; only then is formaldehyde added at a temperature of the mixture preferably in the range from 20 to 120° C., more preferably in the range from 25 to 100° C. and especially preferably in the range from 30 to 90° C., and then converted in a suitable reaction apparatus. The reaction temperature is, as described above, preferably in the range from 20 to 200° C., more preferably in the range from 25 to 170° C., more preferably in the range from 30 to 150° C. and especially preferably in the range from 40 to 140° C.

In a further embodiment, aniline is first mixed with formaldehyde and if appropriate with a solvent in a suitable mixing apparatus, and reacted at a temperature in the range from 5 to 150° C., preferably in the range from 20 to 120° C. and more preferably in the range from 30 to 90° C. Only then is the remaining mixture, if appropriate after suitable intermediate steps, for example distillation or phase separation, contacted with the catalyst, preferably at a temperature in the range from 20 to 200° C. The reaction is again preferably effected at a temperature in the range from 20 to 200° C., more preferably in the range from 25 to 170° C., more preferably in the range from 30 to 150° C. and especially preferably between 40 and 140° C.

In the context of the present invention, it is possible to alter the temperature in the course of the above-described reactions to provide the amine. In this context, it is possible to perform the reaction at two or more temperatures or within two or more temperature ranges, each of which is within the above-specified limits. Temperature alterations in the course of the reaction can be executed continuously or discontinuously. The temperature is preferably increased during the reaction, preferably increased continuously.

Preference is given to purifying the resulting reaction mixture comprising the amine in a suitable manner after the reaction.

As far as the purification of the reaction mixture is concerned, there are generally no restrictions.

In a preferred embodiment, the reaction mixture obtained in each case is neutralized for purification by adding at least one suitable base. Suitable bases are, for example, alkali metal hydroxides such as sodium hydroxide or potassium hydroxide, alkaline earth metal hydroxides or alkaline earth metal oxides, or ammonia. Preference is given to neutralizing the reaction mixture with sodium hydroxide. Preference is further given to effecting the neutralization within a temperature range in the range from 20 to 150° C., more preferably in the range from 30 to 140° C. and especially preferably in the range from 40 to 120° C.

When the reaction mixture is neutralized by adding at least one suitable base, preference is given, in a further step, to removing the aqueous phase from the mixture thus obtained to obtain a mixture comprising the amine. When a neutralization with subsequent phase separation is performed, these individual steps can each be performed once or more than once.

In an alternative embodiment, the amine-comprising mixture is distilled for purification, optionally after performing the at least one neutralization and subsequent phase separation. The distillation is preferably performed at temperatures in the range from 100 to 300° C., preferably in the range from 120 to 260° C. Preference is given to effecting the distillation at a pressure in the range from 1 to 2000 mbar, more preferably in the range from 2 to 1500 mbar.

The exact composition of the resulting optionally purified amine depends on the preparation conditions. For instance, the ratio of the individual diamines and/or polyamines relative to one another can be controlled within wide limits by the selection of different process conditions in the reaction of aniline with formaldehyde. The polyamines of the diphenylmethane series are typically formed by virtue of the reaction not stopping at the diamine, i.e. at the two-ring product, but instead, typically in a decreasing amount, reacting further to give the tricyclic and higher polycyclic products.

Control with regard to obtaining a preferred composition is preferably effected by the establishment of the particular ratio of aniline to formaldehyde or of the particular ratio of the acidic catalyst to the aniline.

Typically, when the amine is provided by reacting formaldehyde with aniline, the amine is obtained in a mixture with further substances. The further substances include, for example, unconverted aniline, unconverted formaldehyde, water and by-products, for example precursors to coloring substances.

The mixture which is obtained from the reaction of aniline with formaldehyde, has optionally been purified as described above and comprises amine can be used directly in (i) as mixture (Gi). The term "directly" means in this context that the mixture obtained from the reaction of aniline with formaldehyde is used in (i) without further intermediate treatment. In this embodiment, the mixture which is obtained from the reaction, has optionally been purified and comprises amine corresponds to the mixture (Gi).

In an alternative embodiment, the mixture obtained from the provision is subjected before (i) to at least one intermediate treatment to obtain the mixture (Gi).

An intermediate treatment is understood to mean, for example, a distillation and/or crystallization and/or neutralization with subsequent water removal of the mixture which is obtained from the reaction, has optionally been purified as described above and comprises amine.

For example, it is possible, as the intermediate treatment, to alter the composition of the amine by enriching individual diamines and/or polyamines, or mixtures of individual diamines, or mixtures of individual polyamines, for example by distillation or crystallization. In addition, individual diamines and/or polyamines and/or mixtures of individual diamines, or mixtures of individual polyamines, can be removed or prepared partly in pure form, and the individual diamines and/or polyamines or mixtures of individual diamines, or mixtures of individual polyamines removed can be used in (i).

Mixture (Gi)

The mixture (Gi) typically comprises at least one precursor to a coloring substance. In this context, the wording "precursor to a coloring substance" means that the conversion of this substance in step (ii), i.e. in the phosgenation stage, results in a coloring substance. For example, the precursor to a coloring substance is formed as a by-product in the reaction of aniline with formaldehyde. Without wishing to make any restriction to specific compounds, examples of such possible precursors include N-formylated diamines and/or N-formylated polyamines of the diphenylmethane series or compounds of the substance class of the 3,4-dihydroquinazolines.

In the context of the invention, an N-formylated diamine or polyamine of the diphenylmethane series is understood to mean diamines or polyamines of the diphenylmethane series which are formylated on one or more amine functionalities, i.e. amines of the following structure

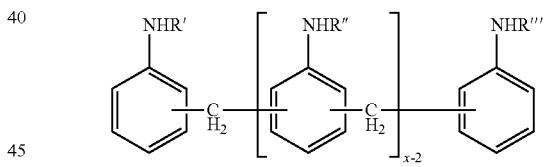

where x = 2 to n where R', R" and R'" are each independently selected from H and formyl, where at least one of the R' or R" or R'" radicals is formyl and n is as defined above.

For example, the mixture (Gi) may comprise an N-formylated diamine selected from the following structures:

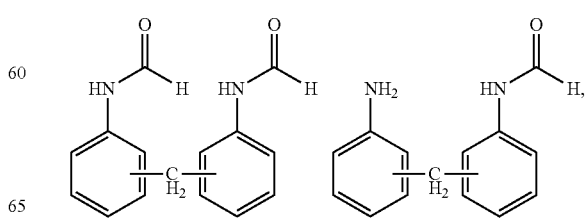

for example a diamine of the following structures:

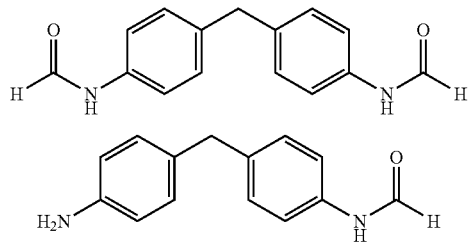

A compound of the substance class of the 3,4-dihydroquinazolines, which are also referred to as 3,4-dihydrazoquinolines in the context of the invention, is understood to mean compounds of the following structure:

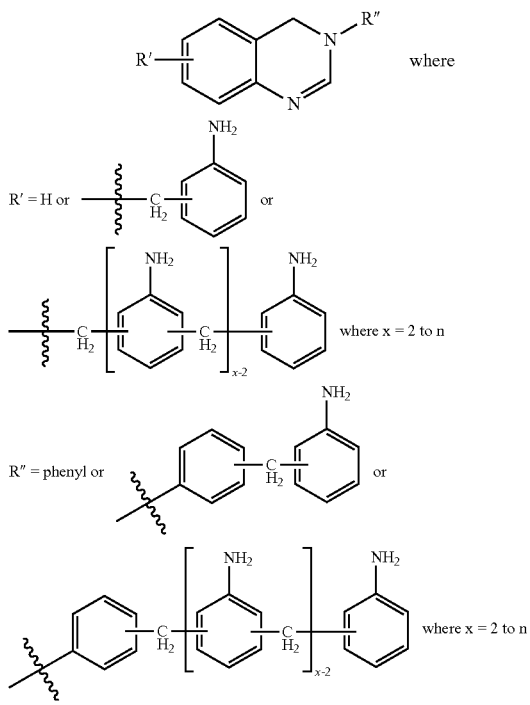

where x is as defined above. For example, the mixture (Gi) comprises one or more compounds selected from compounds of the following structures:

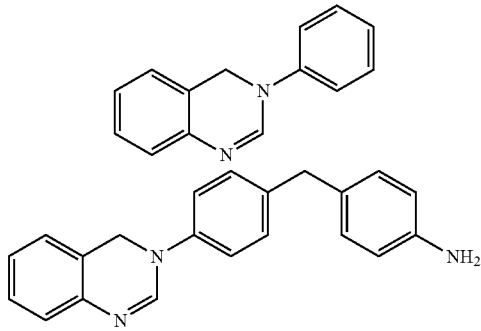

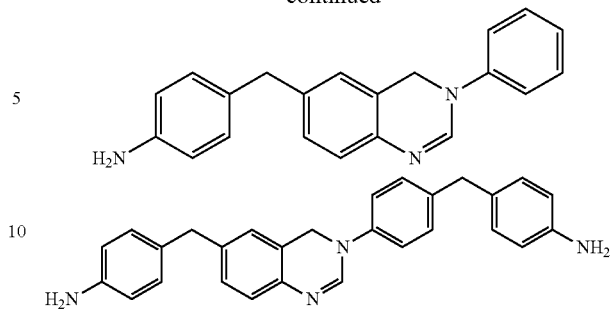

Accordingly, the present invention also relates to a process as described above, wherein the mixture (Gi), in addition to the amine, comprises at least one compound selected from the group consisting of N-formylated diamines of the diphenylmethane series, N-formylated polyamines of the diphenylmethane series and 3,4-dihydroquinazolines. The mixture (Gi) preferably comprises, in addition to the amine, at least one N-formylated diamine of the diphenylmethane series and at least one compound of the substance class of the 3,4-dihydroquinazolines; more preferably, the mixture (Gi) comprises, in addition to the amine, at least one N-formylated diamine of the diphenylmethane series and at least one compound selected from the group consisting of 3-phenyl-3,4-dihydroquinazoline, 3-(4-(4-aminobenzyl)phenyl)-3,4-dihydroquinazoline, 6-(4-aminobenzyl)-3-phenyl-3,4-dihydroquinazoline and 6-(4-aminobenzyl)-3-(4-(4-aminobenzyl)-3,4-dihydroquinazoline.

In a preferred embodiment, the present invention accordingly also describes a process for preparing an isocyanate, comprising
(i) hydrogenating a mixture (Gi) comprising an amine and at least one precursor to a coloring substance, preferably a mixture (Gi) comprising an amine and additionally at least one N-formylated diamine of the diphenylmethane series and/or N-formylated polyamine of the diphenylmethane series and/or at least one compound of the substance class of the 3,4-dihydroquinazolines, in the presence of a copper-comprising hydrogenation catalyst to obtain a mixture (Gii) comprising the amine,
(ii) reacting the mixture (Gii) with phosgene to obtain a mixture (Giii) comprising the isocyanate.

When the mixture (Gi) comprises at least one N-formylated diamine of the diphenylmethane series, the mixture preferably comprises the latter in an amount of at most 5% by weight, preferably in an amount of at most 2% by weight and more preferably in an amount of at most 1% by weight, based in each case on the total weight of the mixture (Gi) and, in the case that the mixture (Gi) comprises more than one N-formylated diamine, based on the sum of all N-formylated diamines.

When the mixture (Gi) comprises at least one N-formylated polyamine of the diphenylmethane series, the mixture preferably comprises the latter in an amount of at most 3% by weight, preferably in an amount of at most 2% by weight and more preferably in an amount of at most 1.5% by weight, based in each case on the total weight of the mixture (Gi).

When the mixture comprises one or more compounds of the substance class of the 3,4-dihydroquinazolines, the mixture comprises the latter in an amount of at most 2%, preferably in an amount of at most 1% and more preferably in an amount of at most 0.5%, based in each case on the total weight of the mixture (Gi), the amount stated being based on the sum of all compounds of the substance class of the 3,4-dihydroquinazolines.

The present invention accordingly also relates to a process wherein the mixture (Gi), in addition to the amine, comprises aniline and at least one compound selected from the group consisting of N-formylated diamines of the diphenylmethane series, N-formylated polyamines of the diphenylmethane series and compounds of the substance class of the 3,4-dihydroquinazolines.

Moreover, the mixture (Gi) may comprise, in addition to the amine, for example, aniline and/or water.

The present invention therefore further describes a process as described above, wherein the mixture (Gi), in addition to the amine, comprises aniline or water or both aniline and water, and at least one compound selected from the group consisting of N-formylated diamines of the diphenylmethane series, N-formylated polyamines of the diphenylmethane series, and compounds of the substance class of the 3,4-dihydroquinazolines.

When the mixture (Gi) comprises aniline, the mixture typically comprises the latter in an amount in the range of up to 75% by weight, preferably in the range of up to 50% by weight, more preferably of up to 40% by weight, based on the total weight of the mixture (Gi).

When the mixture (Gi) comprises water, the mixture typically comprises the latter in an amount in the range of up to 50% by weight, preferably in the range of up to 25% by weight, more preferably in the range of up to 10% by weight, based on the total weight of the mixture (Gi).

In one embodiment, the mixture (Gi) comprises aniline in an amount in the range of up to 50% by weight, preferably in an amount in the range of up to 40% by weight, water in an amount in the range of up to 25% by weight, preferably of up to 10% by weight, at least one N-formylated diamine of the diphenylmethane series in an amount of at most 5% by weight, preferably of at most 2% by weight and more preferably of at most 1% by weight, and at least one compound of the substance class of the 3,4-dihydroquinazolines in an amount of at most 2% by weight, preferably of at most 1% by weight and more preferably of at most 0.5% by weight, based in each case on the total weight of the mixture (Gi).

In a further embodiment, the mixture (Gi) comprises no aniline or no water or neither aniline nor water.

Step (i)

The hydrogenation of the mixture (Gi) in (i) is effected preferably at a temperature in the range from 20 to 300° C., especially preferably at a temperature of 40 to 280° C., more preferably at a temperature in the range from 60 to 240° C. and especially preferably at a temperature in the range from 70 to 200° C. More preferred are ranges from 100 to 220° C., more preferably of 120 to 220° C. and especially preferably of 120 to 200° C. Typically, the hydrogenation in (i) is effected at a pressure in the range from 1 to 300 bar, preferably at a pressure in the range from 10 to 100 bar and more preferably at a pressure in the range from 20 to 50 bar.

Accordingly, the present invention also relates to a process wherein the hydrogenation in (i) is effected at a temperature in the range from 20 to 300° C., preferably 70 to 200° C., more preferably from 100 to 220° C., especially preferably from 120 to 200° C., and at a pressure in the range from 1 to 300 bar, preferably 20 to 50 bar. The present invention likewise relates to a polyisocyanate preparable by this process.

Useful hydrogenation catalysts in (i) in principle include all suitable copper-comprising hydrogenation catalysts. Preference is given to hydrogenation catalysts with a copper content in the range from 0.1 to 100% by weight, more preferably in the range from 1 to 80% by weight, more preferably in the range from 2 to 75% by weight, more preferably in the range from 5 to 70% by weight, more preferably in the range from 10 to 60% by weight, based in each case on the total weight of the hydrogenation catalyst and calculated as the metal.

Accordingly, the present invention also relates to a process as described above wherein the hydrogenation catalyst comprises copper in an amount in the range from 0.1 to 100% by weight, preferably in the range from 10 to 60% by weight, based on the total weight of the hydrogenation catalyst and calculated as the metal. The present invention likewise relates to a polyisocyanate preparable by this process.

The copper may be present in the hydrogenation catalyst as the metal or as a copper compound or as a mixture of at least two copper compounds, or as a mixture of metal and a copper compound or as a mixture of metal and at least two copper compounds. Copper compounds include, for example, preferably copper chromate, copper oxide, copper nitrate, copper sulfate, copper halides, for example copper chloride, copper bromide or copper iodide, copper carbonate, copper acetylacetate, copper alkoxides or copper aryloxides, and copper carboxylates.

Among other catalysts, preference is given in the process according to the invention to using supported hydrogenation catalysts which, as well as copper, comprise at least one support material, which support material may be a support material which is inert or essentially inert under the reaction conditions. The support material is preferably selected from the group consisting of activated carbon, silicon dioxide, aluminum oxides, for example alpha-aluminum oxide, zinc oxide, titanium dioxide, magnesium oxide, manganese oxide, zirconium oxide, iron oxide, lanthanum oxide and mixtures of two or more of these materials. The support material is more preferably selected from the group consisting of silicon dioxide, aluminum oxide, zinc oxide, titanium oxide, manganese oxide, zirconium oxide, lanthanum oxide and a mixture of two or more of these materials.

The term "silicon dioxide" as used in the context of the present invention also comprises silicates, for example sodium silicate.

The present invention accordingly also relates to a process as described above wherein the hydrogenation catalyst comprises a support material selected from the group consisting of silicon dioxide, aluminum oxide, zinc oxide, titanium dioxide, manganese oxide, zirconium oxide, lanthanum oxide and a mixture of two or more of these materials.

In one embodiment of the process according to the invention, the hydrogenation catalyst comprises the at least one support material in an amount of 1 to 99% by weight, preferably of 10 to 95% by weight, more preferably of 25 to 95% by weight, more preferably of 40 to 90% by weight, based in each case on the total weight of the hydrogenation catalyst.

The present invention therefore also relates to the process as described above wherein the hydrogenation catalyst comprises the support material in an amount in the range from 40 to 90% by weight, based on the total weight of the hydrogenation catalyst.

In a preferred embodiment of the present invention, the hydrogenation catalyst comprises, for example, copper, preferably in the form of copper oxide, in an amount in the range from 1 to 80% by weight, preferably in the range from 10 to 70% by weight and more preferably in the range from 30 to 65% by weight, based in each case on the total weight of the hydrogenation catalyst and calculated as the metal, and aluminum oxide in an amount in the range from 20 to 99% by weight, preferably in the range from 30 to 90% by weight and more preferably in the range from 35 to 90% by weight, based in each case on the total weight of the hydrogenation catalyst.

In an alternative preferred embodiment of the present invention, the hydrogenation catalyst comprises, for example, copper, preferably in the form of copper oxide, in an amount in the range from 1 to 80% by weight, preferably in the range from 5 to 60% by weight, more preferably in the range from 10 to 40% by weight, based in each case on the total weight of the hydrogenation catalyst and calculated as the metal, and silicon dioxide in an amount in the range from 20 to 99% by weight, preferably in the range from 40 to 95% by weight and more preferably in the range from 60 to 90% by weight, based in each case on the total weight of the hydrogenation catalyst.

In the context of the present invention, the hydrogenation catalyst may comprise additional elements as well as copper and the at least one support material which may be present in the hydrogenation catalyst. For example, these elements are selected from elements of groups I to VIII of the Periodic Table of the Elements. The hydrogenation catalyst preferably comprises at least one element selected from the group consisting of lanthanum, magnesium, manganese, barium, carbon, chromium, silver, zinc, sodium, gold and a mixture of two or more of these elements.

When the hydrogenation catalyst comprises at least one additional element, it preferably comprises the additional element in an amount in the range from 0.1 to 50% by weight, preferably in the range from 1 to 40% by weight, based in each case on the total weight of the hydrogenation catalyst.

In one embodiment of the present invention, the hydrogenation catalyst comprises copper, preferably in the form of copper oxide, in an amount in the range from 1 to 90% by weight, preferably in the range from 10 to 70% by weight, more preferably in the range from 20 to 50% by weight, based in each case on the total weight of the hydrogenation catalyst and calculated as the metal, and zinc, preferably in the form of zinc oxide, in an amount in the range from 1 to 90% by weight, preferably in the range from 10 to 70% by weight, more preferably in the range from 20 to 50% by weight, based in each case on the total weight of the hydrogenation catalyst and calculated as the metal, and aluminum oxide in an amount in the range from 1 to 60% by weight, preferably in the range from 5 to 50% by weight, more preferably in the range from 10 to 30% by weight, based in each case on the total weight of the hydrogenation catalyst.

In a further embodiment of the present invention, the hydrogenation catalyst comprises copper in an amount in the range from 10 to 80% by weight, preferably in the range from 20 to 75% by weight, more preferably in the range from 40 to 70% by weight, based in each case on the total weight of the hydrogenation catalyst and calculated as the metal, and lanthanum, preferably in the form of lanthanum oxide, in an amount in the range from 0.1 to 20% by weight, preferably in the range from 1 to 10% by weight, more preferably in the range from 2 to 6% by weight, based in each case on the total weight of the hydrogenation catalyst and calculated as the metal, and aluminum oxide in an amount in the range from 1 to 60% by weight, preferably in the range from 5 to 50% by weight and more preferably in the range from 10 to 40% by weight, based in each case on the total weight of the hydrogenation catalyst. The hydrogenation catalyst more preferably comprises the copper as a mixture of metal and copper oxide.

In a further embodiment of the present invention, the hydrogenation catalyst comprises copper, preferably in the form of copper oxide, in an amount in the range from 1 to 80% by weight, preferably in the range from 10 to 60% by weight, more preferably in the range from 20 to 45% by weight, based in each case on the total weight of the hydrogenation catalyst and calculated as the metal, and magnesium, preferably in the form of magnesium oxide, in an amount in the range from 0.1 to 50% by weight, preferably in the range from 1 to 25% by weight, more preferably in the range from 5 to 20% by weight, based in each case on the total weight of the hydrogenation catalyst and calculated as the metal, and silicon dioxide in an amount in the range from 5 to 80% by weight, preferably in the range from 10 to 60% by weight, more preferably in the range from 20 to 50% by weight, based in each case on the total weight of the hydrogenation catalyst.

In a further embodiment of the present invention, the hydrogenation catalyst comprises copper, preferably in the form of copper oxide and/or metallic copper, in an amount in the range from 5 to 90% by weight, preferably in the range from 20 to 80% by weight, more preferably in the range from 40 to 70% by weight, based in each case on the total weight of the hydrogenation catalyst and calculated as the metal, and manganese, preferably in the form of manganese oxide, in an amount in the range from 0.1 to 60% by weight, preferably in the range from 1 to 40% by weight, more preferably in the range from 5 to 20% by weight, based in each case on the total weight of the hydrogenation catalyst and calculated as the metal, and aluminum oxide in an amount in the range from 5 to 80% by weight, preferably in the range from 10 to 60% by weight and more preferably in the range from 20 to 50% by weight, based in each case on the total weight of the hydrogenation catalyst. The hydrogenation catalyst more preferably comprises the copper as a mixture of metallic copper and copper oxide.

The hydrogenation catalyst more preferably additionally comprises at least one element selected from the group consisting of barium, chromium, silver, gold and mixtures thereof, more preferably barium, chromium, or both barium and chromium.

When the catalyst comprises chromium as the at least one additional element, the molar ratio of copper to chromium is preferably in the range from 1:5 to 100:1, more preferably in the range from 1:3 to 50:1 and more preferably in the range from 1:2 to 10:1, in each case calculated as the metal.

In one embodiment of the present invention, the hydrogenation catalyst comprises copper, preferably in the form of copper oxide and copper chromate, in an amount in the range from 1 to 80% by weight, preferably in the range from 10 to 70% by weight, more preferably in the range from 25 to 65% by weight, based in each case on the total weight of the hydrogenation catalyst and calculated as metallic copper, and chromium in an amount in the range from 1 to 60% by weight, preferably in the range from 5 to 50% by weight, more preferably in the range from 10 to 40% by weight, based in each case on the total weight of the hydrogenation catalyst and calculated as the metal, and barium, preferably in the form of barium oxide, in an amount in the range from 0.1 to 40% by weight, preferably in the range from 0.5 to 30% by weight, more preferably in the range from 1 to 20% by weight, based in each case on the total weight of the hydrogenation catalyst and calculated as the metal.

In a further embodiment of the present invention, the hydrogenation catalyst comprises copper, preferably in the form of copper oxide and copper chromate, in an amount in the range from 5 to 70% by weight, preferably in the range from 15 to 60% by weight, more preferably in the range from 30 to 50% by weight, based in each case on the total weight of the hydrogenation catalyst and calculated as metallic copper, and chromium in an amount in the range from 1 to 60% by weight, preferably in the range from 10 to 50% by weight, more preferably in the range from 20 to 40% by weight, based in each case on the total weight of the hydrogenation catalyst and calculated as the metal, and carbon in an amount in the range from 0.1 to 20% by weight, preferably in the range from 0.5 to 10% by weight, more preferably in the range from 1 to 5% by weight, based in each case on the total weight of the hydrogenation catalyst and calculated as the element.

In a further embodiment of the present invention, the hydrogenation catalyst comprises copper, preferably in the form of copper oxide and copper chromate, in an amount in the range from 1 to 80% by weight, preferably in the range from 10 to 60% by weight, more preferably in the range from 20 to 40% by weight, based in each case on the total weight of the hydrogenation catalyst and calculated as metallic copper, and chromium in an amount in the range from 1 to 70% by weight, preferably in the range from 10 to 50% by weight, more preferably in the range from 20 to 40% by weight, based in each case on the total weight of the hydrogenation catalyst and calculated as the metal, and carbon in an amount in the range from 0.1 to 20% by weight, preferably in the range from 0.5 to 10% by weight, more preferably in the range from 1 to 5% by weight, based in each case on the total weight of the hydrogenation catalyst and calculated as the element. More preferably, the catalyst of this embodiment additionally comprises barium and/or sodium, preferably barium and sodium. When the catalyst additionally comprises barium, it comprises barium preferably in an amount in the range from 0.1 to 20% by weight, preferably in the range from 1 to 15% by weight, more preferably in the range from 4 to 10% by weight, based in each case on the total weight of the hydrogenation catalyst and calculated as the metal. When the catalyst additionally comprises sodium, it preferably comprises sodium as sodium silicate in an amount in the range from 0.1 to 20% by weight, preferably in the range from 0.5 to 15% by weight, based in each case on the total weight of the hydrogenation catalyst and calculated as sodium silicate.

In a further embodiment of the present invention, the hydrogenation catalyst comprises copper, preferably in the form of copper oxide and copper chromate, in an amount in the range from 1 to 80% by weight, preferably in the range from 5 to 60% by weight, more preferably in the range from 20 to 50% by weight, based in each case on the total weight of the hydrogenation catalyst and calculated as metallic copper, and chromium in an amount in the from 1 to 80% by weight, preferably in the range from 5 to 60% by weight, more preferably in the range from 20 to 50% by weight, based in each case on the total weight of the hydrogenation catalyst and calculated as the metal, and carbon in an amount in the range from 0.1 to 20% by weight, preferably in the range from 0.5 to 10% by weight, more preferably in the range from 1 to 5% by weight, based in each case on the total weight of the hydrogenation catalyst and calculated as the element. More preferably, the catalyst of this embodiment additionally comprises manganese and/or sodium, preferably manganese and sodium. When the catalyst additionally comprises manganese, it preferably comprises manganese in an amount in the range from 0.1 to 20% by weight, preferably in the range from 0.5 to 10% by weight, more preferably in the range from 1 to 5% by weight, based in each case on the total weight of the hydrogenation catalyst and calculated as the metal. When the catalyst additionally comprises sodium, it preferably comprises sodium in an amount in the range from 0.1 to 10% by weight, preferably in the range from 0.2 to 5% by weight, based in each case on the total weight of the hydrogenation catalyst and calculated as sodium silicate.

The hydrogenation catalysts used in (i) in accordance with the invention are notable for particularly advantageous catalyst lifetimes.

In a preferred embodiment, the hydrogenation catalyst is suitably activated before its use in (i). The activation can generally be effected by all suitable methods known to those skilled in the art. The catalyst is preferably activated by contacting with a mixture comprising hydrogen. The mixture optionally comprises, as well as hydrogen, at least one inert medium, preferably an inert medium selected from the group consisting of nitrogen, helium, argon and mixtures of two or more of these compounds, more preferably nitrogen. This contacting is preferably effected at a temperature in the range from 100 to 300° C., more preferably at a temperature in the range from 125 to 250° C. and especially preferably at a temperature in the range from 150 to 200° C. The temperature can be altered continuously or discontinuously within the ranges specified in the course of activation.

As far as the composition of the mixture used to activate the catalyst is concerned, the proportion of hydrogen in the mixture is preferably increased over the course of activation continuously or discontinuously, for example stepwise. Preference is given to using, for the activation, mixtures comprising a proportion by volume of hydrogen in the inert medium in the range from 0.1 to 100%, preferably in the range from 1 to 100%.

In a preferred embodiment, the hydrogenation catalyst, for example at a temperature in the range from 100 to 300° C., preferably 125 to 250° C. and more preferably of 150 to 200° C., is contacted first with a mixture comprising nitrogen and hydrogen with a hydrogen content in the range from 1% to 50%, preferably in the range from 1% to 25%, then with a mixture comprising nitrogen and hydrogen with a hydrogen content in the range from 1% to 99%, preferably in the range from 1% to 75%, and then with essentially pure hydrogen.

The hydrogenation can be performed by customary methods known to those skilled in the art. For instance, the mixture (Gi), before being contacted with the hydrogenation catalyst, can be admixed with hydrogen, or hydrogen can be added to the solution after the addition of the hydrogenation catalyst. In this case, for example, hydrogen can be injected into the mixture (Gi) after the addition of the hydrogenation catalyst. The hydrogenation can be effected continuously or batchwise, preference being given to a continuous method.

When the hydrogenation in (i) is performed batchwise, it is typically performed for a time within the range from 1 to 48 h, preferably within the range from 4 to 36 h and more preferably within the range from 6 to 24 h. A mass ratio of catalyst to MDA in the range from 1000:1 to 1:1, preferably from 500:1 to 1:1, is typically selected.

When the hydrogenation is performed continuously, the contacting with hydrogen is preferably effected with a GHSV in the range from 0.1 to 1000 h$^{-1}$, preferably in the range from 0.5 to 500 h$^{-1}$, and more preferably in the range from 1 to 100 h$^{-1}$. The GHSV (gas hourly space velocity) is defined as the gas volume (in l) which flows in per hour divided by the volume of the catalyst (in l).

In addition, the catalyst is contacted with the mixture (Gi) at an LHSV in the range from 0.1 to 20 kg/(l*h), preferably in the range from 0.2 to 15 kg/(l*h) and more preferably in the range from 0.5 to 10 kg/(l*h). The LHSV (liquid hourly space velocity) is defined as the mass of the mixture (Gi) (in kg) which flows in per hour divided by the volume of the catalyst (in l).

The hydrogenation in (i) can be performed without solvent or in the presence of at least one solvent. The solvents used may be alcohols, for example linear or branched, aliphatic or aromatic, especially linear or branched, aliphatic or aromatic alcohols having 1 to 18 carbon atoms, especially having 1 to 10 carbon atoms, more preferably having 1 to 5 carbon atoms, for example methanol, ethanol or tert-butanol, and also amines, ethers, aromatics, halogenated aromatics, aromatic amines, dimethylformamide, water, preferably benzene, toluene, ethylbenzene, xylenes, halogenated aromatics, aniline, water, and more preferably monochlorobenzene (MCB) or dichlorobenzenes, such as 1,4-dichlorobenzene, or mixtures of two or more of these compounds. When a solvent is used in (i), preference is given to using a solvent selected from the group consisting of methanol, ethanol, tert-butanol, benzene, toluene, ethylbenzene, ortho-xylene, meta-xylene, para-xylene, monochlorobenzene, 1,4-dichlorobenzene, aniline, water, DMF and mixtures of two or more thereof.

Particular preference is given to performing (i) without adding a solvent.

The hydrogenation catalyst can be used as a fixed bed or suspension catalyst. It may be configured in any desired form, preferably in a form which is suitable for use in fixed bed, moving bed or fluidized bed reactors. The hydrogenation can be effected, for example, continuously in liquid phase mode or trickle mode over a catalyst bed.

When the hydrogenation catalyst is a suspension catalyst, the mixing in suspension mode can be effected, for example, by means of customary stirrers, sparging stirrers, or else by means of static mixers. In a continuous method, the hydrogenation can be effected, for example, in suspension mode in a circulation system by means of nozzle injection with discharge of the catalyst-free product by known methods. In continuous mode over a catalyst bed, it is possible to work, for example, in hydrogen cocurrent or countercurrent.

When the hydrogenation catalyst is used in the form of shaped bodies, the shaping can be effected, for example, by tableting, extrusion, spray drying or spray granulation. The specific geometry of the shaped bodies is generally decided by the process technology requirements which are imposed by the process in which the hydrogenation catalyst is to be used.

Preference is given to performing the hydrogenation until a mixture (Gi) with the desired quality is achieved. The term "desired quality" means in this context that the mixture (Gii) after step (iii) has a better color than the mixture (Gi) after step (iii).

When the mixture (i) comprises at least one compound of the substance class of the 3,4-dihydroquinazolines, the hydrogenation in (i) preferably reacts at least a portion of at least one of these compounds with hydrogen, such that the mixture (Gii) obtained in (i) comprises a smaller amount of the at least one compound than the mixture (Gi). The mixture (Gii) obtained in (i) more preferably no longer comprises any detectable amount of the at least one compound of the substance class of the 3,4-dihydroquinazolines. The term "not detectable" means in this connection that the mixture (Gii) comprises at most 10 ppm, preferably less than 10 ppm, of the particular compounds, the stated amount being based on each individual compound, determined by means of a suitable gas chromatography (GC) method.

When the mixture (i) comprises at least one N-formylated diamine of the diphenylmethane series and/or N-formylated polyamine of the diphenylmethane series, the hydrogenation in (i) preferably reacts a portion of at least one of these compounds with hydrogen, such that the mixture (Gii) obtained in (i) preferably comprises a smaller amount of the at least one compound than the mixture (Gi). The mixture (Gii) obtained in (i) more preferably does not comprise any detectable amounts of the formylated compounds. The term "not detectable" in this context means that the mixture (Gii) comprises at most 50 ppm, preferably less than 50 ppm, of the particular compounds, the amount stated being based on each individual compound, determined by means of a suitable gas chromatography (GC) method.

The at least one N-formylated diamine or the at least one N-formylated polyamine is preferably converted by step (i) to the corresponding diamine or polyamine. This has the advantage that these compounds are then not converted to coloring substances, but instead to the desired isocyanate.

Step (ii)

In one embodiment, the mixture (Gii) obtained in (i) is used directly in (ii), i.e. without further intermediate treatment.

In an alternative embodiment, the mixture (Gii), before the reaction with phosgene in (ii), is subjected to at least one intermediate treatment.

Examples of intermediate treatments include distillation and/or crystallization.

When the mixture (Gii) comprises, for example, undesired low boilers, for example water or aniline, it is possible, for example, to remove at least a portion of the low boilers from (Gii) before step (ii). Preference is given to removing low boilers present in (Gii) by distillation before step (ii).

When the hydrogenation in (i) is performed in the presence of at least one solvent, for example, preference is given to removing at least a portion of the solvent, preferably essentially all of the solvent, from the mixture (Gii) before it is used in (ii). Such a removal can be effected, for example, by distillation. It is equally possible in principle not to remove the solvent and to use the entire mixture (Gii) in (ii).

In addition, it is possible to blend the mixture (Gii) with other MDA fractions. For example, one or more diamines or else polyamines can be added, which can be provided, for example, in the form of an already hydrogenated fraction, or can be obtained, for example, by distillation or crystallization from (Gi).

The mixture (Gii) obtained in (i) is preferably treated by distillation before the reaction with phosgene in (ii); more preferably, low boilers and/or solvents are removed by at least one distillation.

Accordingly, the present invention also relates to a process for preparing an isocyanate, comprising
(i) hydrogenating a mixture (Gi) comprising an amine in the presence of a hydrogenation catalyst comprising copper to obtain a mixture (Gii) comprising the amine;
(ii) reacting the mixture (Gii) with phosgene to obtain a mixture (Giii) comprising the isocyanate,
wherein the mixture (Gii) obtained in (i), before the reaction with phosgene in (ii), is subjected to at least one intermediate treatment, preferably a distillation.

The reaction with phosgene is effected typically at temperatures in the range from 20 to 250° C., preferably in the range from 30 to 200° C., more preferably in the range from 40 to 175° C. and especially preferably in the range from 50 to 150° C.

It is possible to alter the temperature in the course of the reaction in step (ii). It is possible here to perform the reaction at two or more temperatures or in two or more temperature ranges, each of which is within the limits specified above. Temperature alterations in the course of (ii) can be implemented continuously or discontinuously.

The reaction in (ii) is effected preferably at pressures in the range from 1 bar to 50 bar, preferably at pressures in the range from 1 bar to 20 bar, more preferably in the range from 1 bar to 15 bar, especially preferably in the range from 1 bar to 12 bar, in particular in the range from 1 bar to 10 bar.

It is possible to alter the pressure in the course of the reaction in step (ii). It is possible here to perform the reaction at two or more pressures or in two or more pressure ranges, each of which is within the limits specified above. Pressure alterations in the course of the reaction can be implemented continuously or discontinuously.

Preference is given to effecting the conversion of phosgene in (ii) in a reactor, for example in a stirred tank, tubular reactor or tube bundle reactor. Preference is given to effecting the conversion in a tubular reactor.

The reaction with phosgene is optionally performed in the presence of at least one solvent. The solvents used may be all inert aromatic, aliphatic or cyclic hydrocarbons or halogenated hydrocarbons which are known for the phosgenation process, in which the particular isocyanate is soluble and which are not attacked under the reaction conditions of the phosgenation. Examples of such solvents are aromatic compounds, for example mono- and dichlorobenzene, toluenes, xylenes and naphthalene derivates, alkanes having 5 to 12 carbon atoms, for example hexane, heptane, octane, nonane, decane, cycloalkanes, for example cyclohexane, inert esters and inert ethers, for example ethyl or butyl acetate, tetrahydrofuran, dioxane or diphenyl ether. Particular preference is given to using a solvent selected from the group consisting of chlorobenzenes and hydrocarbons. Particular preference is given to using monochlorobenzene as the solvent.

The present invention accordingly also relates to a process as described above wherein (ii) is performed in the presence of a solvent, preferably in the presence of a solvent selected from the group consisting of chlorobenzenes and hydrocarbons, most preferably in monochlorobenzene. The present invention likewise relates to an isocyanate preparable by this process.

In the process according to the invention, in (ii), preferably a molar ratio of phosgene to amine in the range from 1:1 to 15:1, preferably 1.2:1 to 10:1, more preferably 1.3:1 to 6:1, is selected.

The reaction in (ii) can optionally be performed in the presence of at least one inert medium. The inert medium is a medium which is typically present in gaseous form at the reaction temperature and does not react with the reactants. The inert medium is generally mixed before the reaction with the mixture (Gii) and/or phosgene. The inert medium is preferably selected from the group consisting of nitrogen, helium, argon, SF6 and mixtures of two or more of these compounds. When an inert medium is used, particular preference is given to using nitrogen.

When an inert medium is used, it is preferably used in an amount in the range from 0.1 to 99.9 percent by volume, preferably in the range from 1.0 to 99.0 percent by volume and more preferably in the range from 10 to 90 percent by volume, based in each case on the total volume of the mixture (Gii) to be reacted with phosgene.

Accordingly, the present invention also relates to a process for preparing an isocyanate, comprising
(i) hydrogenating a mixture (Gi) comprising an amine in the presence of a hydrogenation catalyst comprising copper to obtain a mixture (Gii) comprising the amine;
(ii) reacting the mixture (Gii) with phosgene in the presence of at least one inert medium to obtain a mixture (Giii) comprising the isocyanate.

The reaction in (ii) can be performed continuously or batchwise.

When the reaction in (ii) is performed batchwise, it is typically performed for a time in the range from 30 seconds to 10 hours, preferably in the range from 1 min to 5 hours and more preferably in the range from 2 min to 2 hours.

When the reaction in (ii) is performed continuously, the reaction with phosgene is preferably performed with a GHSV in the range from $0.1$ millis$^{-1}$ to $10\,\text{h}^{-1}$, preferably in the range from 1 millis$^{-1}$ to 1 h$^{-1}$, more preferably in the range from 3 millis$^{-1}$ to 30 min$^{-1}$.

The term "isocyanate" used in the context of the present invention denotes, correspondingly to the term "amine" explained above, at least one polyisocyanate and/or at least one diisocyanate. Accordingly, the term "isocyanate" means, for example, a diisocyanate, or a polyisocyanate, or a mixture of a diisocyanate and a polyisocyanate, or a mixture of at least two diisocyanates, or a mixture of at least two polyisocyanates, or a mixture of at least two diisocyanates and of at least two polyisocyanates, or a mixture of at least two diisocyanates and of a polyisocyanate, or a mixture of at least two diisocyanates and at least two polyisocyanates.

The isocyanate is more preferably selected from a diisocyanate of the diphenylmethane series, from a mixture of two or more diisocyanates of the diphenylmethane series, from a polyisocyanate of the diphenylmethane series, from a mixture of at least two polyisocyanates of the diphenylmethane series, and from a mixture of one or more diphenyl diisocyanates of the diphenylmethane series with one or more polyisocyanates of the diphenylmethane series.

The isocyanate is most preferably a mixture of at least two diisocyanates of the diphenylmethane series and at least two polyisocyanates of the diphenylmethane series.

The present invention accordingly also relates to a process as described above, wherein the amine is a mixture of two or more diamines of the diphenylmethane series and two or more polyamines of the diphenylmethane series, and the isocyanate is a mixture of two or more diisocyanates of the diphenylmethane series and two or more polyisocyanates of the diphenylmethane series.

The present invention likewise relates to an isocyanate preparable by the process, wherein the isocyanate is a mixture of two or more diisocyanates of the diphenylmethane series and two or more polyisocyanates of the diphenylmethane series.

In the reaction in (ii), the isocyanate may form in a mixture with further constituents.

The mixture obtained in (ii) typically comprises further constituents, for example solvents and/or phosgene and/or hydrogen chloride and/or impurities, for example small amounts of coloring substances or chlorine or chlorinated compounds. One example of chlorinated compounds is carbamoyl chlorides.

The isocyanate mixture obtained can be worked up in a customary manner known to those skilled in the art. For example, the mixture can be washed with a solvent. Preferred solvents include, for instance, hydrocarbons, for example chlorobenzene, dichlorobenzene or toluene.

In addition, the further constituents or at least some of the further constituents can be removed from the polyisocyanate in a suitable manner. For example, the further constituents can be removed from the polyisocyanate by means of at least one distillation. In this context, the term "at least one distillation" means that it is possible to perform one or more distillations, each of which may be performed at the same or different temperatures and in the same or different pressure ranges. When a solvent is used in (ii), preference is given to removing at least the solvent from the mixture obtained in (ii) by distillation.

The optionally suitably purified isocyanate obtained in (ii) preferably has a total chlorine content of at most 9000 ppm, more preferably of at most 8000 ppm, more preferably of at most 7000 ppm and especially preferably of at most 6000 ppm.

Accordingly, the present invention also relates to a polyisocyanate preparable by a process as described above with a total chlorine content, determined to ASTM D4661-98, of at most 9000 ppm, more preferably of at most 6000 ppm.

In addition, the optionally suitably purified isocyanate obtained in (ii) preferably has a content of difficulty hydrolyzable chlorine (DHC) of at most 9000 ppm, preferably of at most 5000 and more preferably of at most 4000 ppm, determined to ASTM D 4663-87.

In addition, the optionally suitably purified isocyanate obtained in (ii) preferably has a content of easily hydrolyzable chlorine (EHC) of at most 1000 ppm, preferably of at most 500 ppm, more preferably of at most 300 ppm, determined to ASTM D 4667-87.

Accordingly, the present invention also relates to an isocyanate preparable by the process as described above with a total chlorine content determined to ASTM D4661-98 of at most 6000 ppm, with a content of difficulty hydrolyzable chlorine (DHC) determined to ASTM D 4663-87 of at most 4000 ppm, and with a content of easily hydrolyzable chlorine (EHC) determined to ASTM D 4667-87 of at most 300 ppm.

The inventive polyisocyanates preferably have a color number L* measured to DIN 5033 of at least 90, preferably of at least 92.5, more preferably of at least 95.

The present invention accordingly also relates to a polyisocyanate preparable by a process as described above with an L* value of at least 95 determined to DIN 5033.

The inventive polyisocyanates preferably have a color number b* measured to DIN 5033 of at most 40, preferably of at most 30, most preferably of at most 25.

Accordingly, the present invention also relates to a polyisocyanate preparable by a process as described above with a b* value of at most 25 determined to DIN 5033.

Accordingly, the present invention also relates to an isocyanate preparable by a process as described above with a color number measured to DIN 5033 with a b* value of at most 25 and an L* value of least 95.

More preferably, in the context of the present invention, preferred values for the total chlorine content, EHC, DHC, b* and L* are obtained simultaneously when the hydrogenation in step (i) is selected at temperatures in the range from 100 to 220° C., more preferably in the range from 120 to 220° C. and especially 120 to 200° C. By way of example, mention should be made, for instance, of the following preferred temperature ranges: 100 to 220° C. or 120 to 220° C. or 140 to 220° C. or 160 to 220° C. or 180 to 220° C. or, for instance, 100 to 200° C. or 120 to 200° C. or 140 to 200° C. or 160 to 200° C. or 180 to 200° C.

In principle, the inventive polyisocyanates or the polyisocyanates prepared or preparable in accordance with the invention can be converted to all conceivable compounds. The inventive polyisocyanates or the polyisocyanates prepared or preparable in accordance with the invention are more preferably used as starting materials for preparing polyurethanes.

The present invention therefore also relates to the use of the inventive polyisocyanates or of the polyisocyanates prepared or preparable in accordance with the invention for preparing polyurethanes.

The invention will be illustrated in detail hereinafter with reference to the examples which follow.

EXAMPLES

I. General Method

I.1 Hydrogenation

In a tubular reactor, 50 ml of a catalyst are installed and activated. The particular catalyst is specified explicitly with regard to its composition in the examples and comparative examples below.

All copper and nickel/copper catalysts were treated for activation, at 180° C. for 18 h in each case, with 1.5 l (STP)/h (standard liters/h) of $H_2$ and 100 l (STP)/h of $N_2$, then with 10 l (STP)/h of $H_2$ and 100 l (STP)/h of $N_2$ for 3 hours, and finally with 10 l (STP)/h of $H_2$ for 3 hours.

All palladium, ruthenium and rhodium catalysts were treated, for activation, in each case at room temperature for 18 h, with 2 l (STP)/h of $H_2$ and 50 l (STP)/h of $N_2$, then with 10 l (STP)/h of $H_2$ and 50 l (STP)/h of $N_2$ for 3 hours, and finally with 10 l (STP)/h of $H_2$ for 3 hours.

After the activation, 25 ml/h of MDA were passed continuously over the catalyst in liquid phase mode at pressure 30 bar and at various temperatures. Hydrogen was metered in at 2 l (STP)/h. In the case that MDA which comprised aniline and/or water was used, the discharge was freed of water and aniline on a rotary evaporator (1 mbar, 160° C., 2 h) and then phosgenated according to method I.2 below. In the case that MDA without low boilers was used, it was phosgenated directly according to method I.2.

I.2 Phosgenation 140 g of gaseous phosgene in 1300 ml of MCB were condensed into a charge vessel and then heated to 35 to 50° C.

70.0 g of MDA in 1300 ml of MCB were introduced under argon from a reservoir vessel into the charge vessel. After the addition of the amine, the temperature was increased to 105 to 125° C. Once all solids had dissolved, phosgene was distilled off under standard pressure. Subsequently, the MCB was distilled off at a pressure of 100 mbar and at 60° C.

After venting with argon, the crude isocyanate was freed of residual MCB at an oil bath temperature of 100° C. and pressure 10 mbar and then heated to 100° C. at 10 mbar for 45 min. Thereafter, the mixture was heated to 180° C. at 10 mbar for 1 h.

The color number of the sample thus obtained was measured to DIN 5033 with a Dr. Lange LICO 200 instrument, and the chlorine content was determined, the total chlorine content (TC) having been determined to ASTM D4661-98, the content of difficulty hydrolyzable chlorine (DHC) to ASTM D 4663-87, and the content of easily hydrolyzable chlorine (EHC) to ASTM D 4667-87.

Comparative Example 1

Untreated MDA (MDA-1; 0.17% by weight of 2,2'-MDA; 4.25% by weight of 2,4'-MDA; 41.13% by weight of 4,4'-MDA; 19.25% by weight of 3-ring MDA; 18.78% by weight of higher oligomers; 13.9% by weight of aniline; 2.2% by weight of water; 0.12% by weight of N-formyl-MDA; 449 ppm 3,4-dihydroquinazolines) was phosgenated according to standard method I.2. MDI was obtained with color numbers L*=74.0 and b*=42.8 and the following chlorine contents: TC 2000 ppm, DHC 800 ppm, EHC 150 ppm.

Comparative Example 2

Untreated crude MDA (MDA-2; 0.22% by weight of 2,2'-MDA; 5.26% by weight of 2,4'-MDA; 50.44% by weight of 4,4'-MDA; 23.68% by weight of 3-ring MDA; 23.31% by weight of higher oligomers; 0.16% by weight of N-formyl-MDA; 421 ppm of 3,4-dihydroquinazolines) was treated as in comparative example 1. This resulted in color numbers of L*=74.2 and b*=58.1. The following chlorine contents were obtained: TC 1700 ppm, DHC 800 ppm, EHC 220 ppm.

Comparative Example 3

Untreated crude MDA (MDA-3; 0.50% by weight of 2,2'-MDA; 9.13% by weight of 2,4'-MDA; 58.23% by weight of 4,4'-MDA; 21.00% by weight of 3-ring MDA; 10.20% by weight of higher oligomers; 0.12% by weight of N-formyl-MDA; 512 ppm of 3,4-dihydroquinazolines) was treated as in comparative example 1. This resulted in color numbers of L*=71.0 and b*=60.2. The following chlorine contents were obtained: TC 1800 ppm, DHC 900 ppm, EHC 190 ppm.

Accordingly, the conversion of the amine in step (ii) without pretreatment results in acceptable chlorine values, but in poor colors.

Comparative Example 4

The preparation was effected according to general methods I.1 and I.2, except that the catalyst used in I.1 was 0.25% by weight of palladium on aluminum oxide. The MDA used was MDA-1. The color numbers and chlorine values obtained at the particular temperatures are reported in the following table:

| Hydrogenation temperature [° C.] | L* | b* | TC [ppm] | DHC [ppm] | EHC [ppm] |
|---|---|---|---|---|---|
| 140 | 89.9 | 53.2 | 8100 | 1800 | 270 |
| 160 | 92.4 | 41.8 | 12100 | 4600 | 510 |
| 180 | 92.8 | 53.9 | 16400 | 7500 | 960 |
| 200 | 89.2 | 80.0 | 22300 | 14300 | 1800 |
| 220 | 87.2 | 93.1 | 22400 | 14500 | 1900 |

Comparative Example 5

The preparation was effected according to general methods I.1 and I.2, except that the catalyst used in I.1 was 0.15% Pd on aluminum oxide. The MDA used was MDA-1. The color numbers and chlorine values obtained at the particular temperatures are reported in the following table:

| Hydrogenation temperature [° C.] | L* | b* | Total chlorine [ppm] | DHC [ppm] | EHC [ppm] |
|---|---|---|---|---|---|
| 100 | 92.1 | 69.4 | 6800 | 1200 | 250 |
| 120 | 92.5 | 54.8 | 8400 | 3800 | 310 |
| 140 | 92.8 | 44.4 | 9000 | 4100 | 320 |
| 160 | 92.2 | 48.6 | 12000 | 6900 | 840 |
| 180 | 92.2 | 68.0 | 16500 | 9000 | 1220 |

Comparative Example 6

The preparation was effected according to general methods I.1 and I.2, except that the catalyst used in I.1 was 5% ruthenium on titanium dioxide. The MDA used was MDA-1. The color numbers and chlorine values obtained at the particular temperatures are reported in the following table:

| Hydrogenation temperature [° C.] | L* | b* | Total chlorine [ppm] | DHC [ppm] | EHC [ppm] |
|---|---|---|---|---|---|
| 95 | 84.3 | 48.2 | 4500 | 900 | 200 |
| 110 | 89.8 | 47.0 | 6400 | 1100 | 250 |
| 125 | 84.8 | 47.8 | 7100 | 1200 | 270 |

In addition, up to 3% ring-hydrogenated products were detected.

Comparative Example 7

The preparation was effected according to general methods I.1 and I.2, except that the catalyst used in I.1 was 1% rhodium on carbon. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 77.2 | 53.6 | 1700 | 880 | 220 |
| 120 | 79.1 | 70.8 | 2000 | 940 | 230 |
| 140 | 80.9 | 46.9 | 2100 | 1380 | 200 |
| 160 | 85.4 | 46.1 | 2100 | 1560 | 250 |
| 180 | 86.2 | 40.9 | 2200 | 1880 | 240 |
| 200 | 86.2 | 45.3 | 4400 | 2870 | 350 |
| 220 | 89.2 | 67.9 | 7300 | 6460 | 420 |

The use of hydrogenation catalysts described in the literature (Pd, Ru, Rh, CE4-7) thus results in somewhat improved L* values compared to untreated mixture, but the b* values remain poor and some of the chlorine values increase significantly.

Example 1

The preparation was effected according to general methods I.1 and I.2, except that the catalyst used in I.1 was a catalyst with the composition 60% CuO, 10% $Mn_2O_3$ and 30% aluminum oxide. The MDA used was MDA-1. The color numbers and chlorine values obtained at the particular temperatures are reported in the following table:

| Hydrogenation temperature [° C.] | L* | b* | Total chlorine [ppm] | DHC [ppm] | EHC [ppm] |
|---|---|---|---|---|---|
| 100 | 78.2 | 45.9 | 2000 | 1490 | 240 |
| 120 | 85.0 | 39.9 | 1900 | 1430 | 250 |
| 140 | 88.0 | 32.4 | 2100 | 1480 | 180 |
| 160 | 91.9 | 25.4 | 1900 | 1740 | 190 |
| 180 | 94.3 | 25.1 | 2800 | 2430 | 190 |
| 200 | 95.7 | 16.6 | 4100 | 3370 | 180 |
| 220 | 94.9 | 24.9 | 7000 | 5440 | 230 |

Example 2

The preparation was effected according to general methods I.1 and I.2, except that the catalyst used in I.1 was a catalyst with the composition 57% CuO, 15% Cu, 24% aluminum oxide, 4% $La_2O_3$. The MDA used was MDA-1. The color numbers and chlorine values obtained at the particular temperatures are reported in the following table:

| Hydrogenation temperature [° C.] | L* | b* | Total chlorine [ppm] | DHC [ppm] | EHC [ppm] |
|---|---|---|---|---|---|
| 160 | 90.4 | 33.9 | 3400 | 1110 | 180 |
| 180 | 96.9 | 22.8 | 3500 | 2400 | 190 |
| 200 | 97.1 | 18.8 | 4100 | 4110 | 180 |
| 220 | 95.7 | 22.9 | 7200 | 6230 | 200 |

Example 3

The preparation was effected according to general methods I.1 and I.2, except that the catalyst used in I.1 was a catalyst with the composition 57% CuO, 15% Cu, 24% aluminum oxide, 4% $La_2O_3$. The MDA used was MDA-3. At a hydrogenation temperature of 160° C., after phosgenation, color numbers of L*=98.2 and b*=11.3 were obtained. This resulted in chlorine values of TC=1900 ppm, DHC=1250 ppm and EHC=140 ppm.

Example 4

The preparation was effected according to general methods I.1 and I.2, except that the catalyst used in I.1 was a catalyst with the composition 25% CuO, 68% $CuCrO_4$, 7% BaO. The MDA used was MDA-1. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 79.5 | 49.5 | 2000 | 1080 | 210 |
| 120 | 88.7 | 36.8 | 2100 | 1020 | 210 |
| 140 | 89.1 | 34.9 | 2200 | 1040 | 200 |
| 160 | 92.7 | 26.3 | 2500 | 1060 | 190 |
| 180 | 96.0 | 17.4 | 2600 | 1280 | 140 |
| 200 | 97.5 | 15.6 | 3100 | 1450 | 170 |
| 220 | 96.8 | 24.7 | 6400 | 4580 | 330 |

Example 5

The preparation was effected according to general methods I.1 and I.2, except that the catalyst used in I.1 was a catalyst with the composition 40% CuO and 40% ZnO and 20% aluminum oxide. The MDA used was MDA-1. The color numbers and chlorine values obtained at the particular temperatures are reported in the following table:

| Hydrogenation temperature [° C.] | L* | b* | Total chlorine [ppm] | DHC [ppm] | EHC [ppm] |
|---|---|---|---|---|---|
| 100 | 85.2 | 38.7 | 2500 | 1170 | 260 |
| 120 | 94.8 | 19.9 | 2400 | 1150 | 200 |
| 140 | 97.5 | 15.4 | 2700 | 1300 | 240 |
| 160 | 97.0 | 16.2 | 3700 | 1570 | 200 |
| 180 | 97.2 | 25.3 | 4400 | 2510 | 240 |
| 200 | 98.0 | 18.8 | 5700 | 4010 | 280 |
| 220 | 98.2 | 17.0 | 11000 | 9000 | 300 |

Example 6

The preparation was effected according to general methods I.1 and I.2, except that the catalyst used in I.1 was a catalyst with the composition 25% CuO on $SiO_2$. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 80 | 80.2 | 51.8 | 1800 | 1220 | 230 |
| 100 | 81.0 | 51.4 | 1700 | 1380 | 220 |
| 120 | 82.0 | 49.1 | 1900 | 1250 | 210 |
| 140 | 88.6 | 36.0 | 2400 | 1430 | 240 |
| 160 | 94.1 | 23.4 | 2600 | 1600 | 240 |
| 180 | 96.7 | 16.8 | 3100 | 1820 | 220 |
| 200 | 97.1 | 20.5 | 4000 | 2190 | 250 |

Example 7

The preparation was effected according to general methods I.1 and I.2, except that the catalyst used in I.1 was a catalyst with the composition 45% CuO, 20% MgO, 35% $SiO_2$. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 81.1 | 48.6 | 1900 | 910 | 230 |
| 120 | 89.1 | 33.6 | 1900 | 1030 | 230 |
| 140 | 90.8 | 25.2 | 1800 | 1290 | 180 |
| 160 | 91.0 | 28.3 | 2000 | 1370 | 170 |
| 180 | 97.3 | 16.2 | 2000 | 1410 | 140 |
| 200 | 96.8 | 20.6 | 3600 | 2670 | 160 |

Example 8

The preparation was effected according to general methods I.1 and I.2, except that the catalyst used in I.1 was a catalyst with the composition 61% CuO on 39% $Al_2O_3$. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 78.3 | 44.8 | 2800 | 960 | 260 |
| 120 | 83.0 | 37.6 | 1800 | 1050 | 230 |
| 140 | 89.1 | 29.5 | 1600 | 1160 | 250 |
| 160 | 95.0 | 19.0 | 1900 | 1440 | 180 |
| 180 | 96.9 | 17.2 | 2300 | 2180 | 170 |
| 200 | 98.0 | 15.5 | 3900 | 4330 | 200 |
| 220 | 96.9 | 49.6 | 5200 | 8570 | 310 |

Example 9

The preparation was effected according to general methods I.1 and I.2, except that the catalyst used in I.1 was a catalyst with the composition 25% CuO, 73% $CuCr_2O_4$, 2% C. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 120 | 83.9 | 42.7 | 2800 | 900 | 240 |
| 140 | 86.2 | 41.4 | 1500 | 960 | 180 |
| 160 | 89.0 | 25.3 | 1700 | 1070 | 170 |
| 180 | 93.6 | 25.7 | 2000 | 1430 | 180 |
| 200 | 90.8 | 44.2 | 3500 | 2270 | 150 |
| 220 | 94.6 | 41.1 | 5700 | 5870 | 250 |

Example 10

The preparation was effected according to general methods I.1 and I.2, except that the catalyst used in I.1 was a catalyst with the composition 19% CuO, 55% $CuCr_2O_4$, 12% $BaCrO_4$, 12% $Na_2SiO_3$, 2% C. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 72.5 | 49.3 | 1400 | 870 | 230 |
| 120 | 75.3 | 44.4 | 1400 | 850 | 170 |
| 140 | 82.2 | 33.9 | 1500 | 950 | 200 |
| 160 | 83.8 | 29.1 | 1600 | 1030 | 200 |
| 180 | 92.4 | 19.8 | 1700 | 1230 | 150 |
| 200 | 96.7 | 17.8 | 2800 | 1790 | 140 |
| 220 | 96.6 | 24.9 | 3700 | 2900 | 130 |

Example 11

The preparation was effected according to general methods I.1 and I.2, except that the catalyst used in I.1 was a catalyst with the composition 33% CuO, 40% $Cr_2O_3$, 16% $CuCr_2O_4$, 5% $MnO_2$, 4% $Na_2SiO_3$, 2% C. The MDA used was MDA-2. The color numbers and chlorine values obtained at the particular temperatures are reported in the table.

| Hydrogenation temperature [° C.] | L* | b* | Total chlorine [ppm] | DHC [ppm] | EHC [ppm] |
|---|---|---|---|---|---|
| 100 | 75.5 | 44.4 | 3400 | 930 | 290 |
| 120 | 77.0 | 44.2 | 1400 | 870 | 210 |
| 140 | 86.6 | 34.6 | 1600 | 1040 | 220 |
| 160 | 81.1 | 28.2 | 2000 | 1130 | 140 |
| 180 | 96.5 | 19.2 | 2800 | 1910 | 180 |
| 200 | 96.4 | 21.4 | 3300 | 2840 | 220 |
| 220 | 96.4 | 23.0 | 5600 | 4600 | 220 |

Example 12

A reactor was charged with 40 ml of a catalyst with the composition 57% CuO, 15% Cu, 24% aluminum oxide, 4% $La_2O_3$, and activated as in general method I.1. Subsequently, MDA-1 was conducted over the catalyst at 25 ml/h in trickle mode at 150° C. and pressure 30 bar. In addition, hydrogen was metered in at 10 l (STP)/h. The total run time was 4200 hours, and samples were taken at regular intervals. These were freed of water and aniline on a rotary evaporator (1 mbar, 160° C., 2 h) and phosgenated according to general procedure I.2. The color numbers and chlorine values of the phosgenated samples are listed in the following table:

| Run time [h] | L* | b* | Total chlorine [ppm] | DHC [ppm] | EHC [ppm] |
|---|---|---|---|---|---|
| 240 | 94.8 | 20.7 | 1960 | 1320 | 170 |
| 1080 | 94.0 | 23.2 | 2100 | 1120 | 200 |
| 2360 | 95.3 | 21.0 | 2040 | 1240 | 170 |
| 3540 | 93.3 | 25.2 | 2100 | 1030 | 180 |
| 4200 | 93.5 | 24.8 | 2050 | 1010 | 200 |

The use of the inventive copper catalysts results, as the examples show, especially at the abovementioned preferred hydrogenation temperatures, in the preferred color numbers, most of which are at values of L*>90 and b*<40, while the chlorine values are simultaneously also within the desired ranges and the total chlorine content TC is for the most part <6000 ppm and the DHC for the most part <5000 ppm.

The invention claimed is:

1. A process for preparing an isocyanate, comprising
    (i) hydrogenating a first mixture (Gi) comprising an amine and at least one precursor to a coloring substance in the presence of a hydrogenation catalyst comprising copper to obtain a second mixture (Gii) comprising the amine and a smaller amount of said at least one precursor to a coloring substance than in said first mixture (Gi);
    (ii) reacting the second mixture (Gii) with phosgene to obtain a third mixture (Giii) comprising the isocyanate,
    wherein said amine is at least one amine selected from the group consisting of a polyamine and a diamine,
    wherein said diamine is at least one selected from the group consisting of phenyldiamine, tolyldiamine, naphthylenediamine, diphenylmethanediamine and
    wherein said polyamine is at least one polycyclic or higher molecular weight derivative of a diamine selected from the group consisting of phenyldiamine, tolyldiamine, naphthylenediamine, diphenylmethanediamine and a mixture thereof.

2. The process of claim 1, wherein the hydrogenation catalyst comprises copper in an amount in a range from 0.1 to 100% by weight, based on a total weight of the catalyst and calculated as the metal.

3. The process of claim 1, wherein the hydrogenation catalyst comprises at least one support material selected from the group consisting of silicon dioxide, aluminum oxide, zinc oxide, titanium dioxide, manganese oxide, zirconium oxide, and lanthanum oxide.

4. The process of claim 3, wherein the hydrogenation catalyst comprises the support material in an amount in a range from 40 to 90% by weight, based on a total weight of the hydrogenation catalyst.

5. The process of claim 1, wherein the hydrogenation catalyst, in addition to copper, further comprises at least one element selected from the group consisting of lanthanum, magnesium, manganese, barium, carbon, chromium, silver, zinc, sodium, and gold.

6. The process of claim 1, wherein the amine is a mixture of at least two diamines of the diphenylmethane series and at least two polyamines of the diphenylmethane series, and the isocyanate is a mixture of at least two diisocyanates of the diphenylmethane series and at least two polyisocyanates of the diphenylmethane series.

7. The process of claim 1, wherein the first mixture (Gi) further comprises aniline or water or aniline and water.

8. The process of claim 7, wherein the first mixture (Gi) comprises aniline in an amount in a range of up to 75% by weight.

9. The process of claim 7, wherein the first mixture (Gi) comprises water in an amount in a range of up to 50% by weight, based on a total weight of the first mixture (Gi).

10. The process of claim 1, wherein the hydrogenating in (i) is effected at a temperature in the range from 20 to 300° C. and a pressure in the range from 1 to 300 bar.

11. The process of claim 1, wherein the reacting in (ii) is effected at a temperature in a range from 100 to 350° C. and at a pressure in a range from 0.5 to 150 bar.

12. The process of claim 1, wherein the first mixture (Gi) further comprises at least one compound selected from the group consisting of an N-formylated diamine of the diphenylmethane series, an N-formylated polyamine of the diphenylmethane series, and a 3,4-dihydroquinazoline.

13. The process of claim 1, wherein the reacting in (ii) is performed in the presence of a solvent.

14. The process of claim 1, wherein said isocyanate has a total chlorine content, determined to ASTM D4661-98, of at most 9000 ppm.

15. The process of claim 1, wherein said isocyanate has a content of difficulty hydrolyzable chlorine (DHC), determined to ASTM D 4663-87, of at most 9000 ppm.

16. The process of claim 1, wherein said isocyanate has a content of easily hydrolyzable chlorine (EHC), determined to ASTM D 4667-87, of at most 1000 ppm.

17. The process of claim 1, wherein said isocyanate has a b* value, determined to DIN 5033, of at most 40.

18. The process of claim 1, wherein said isocyanate has an L* value, determined to DIN 5033, of at least 90.

* * * * *